(12) United States Patent
Minamino et al.

(10) Patent No.: US 12,133,721 B2
(45) Date of Patent: Nov. 5, 2024

(54) PULSE-WAVE SIGNAL ANALYSIS DEVICE, PULSE-WAVE SIGNAL ANALYSIS METHOD AND COMPUTER PROGRAM

(71) Applicant: National University Corporation Kagawa University, Kagawa (JP)

(72) Inventors: Tetsuo Minamino, Kagawa (JP); Kazuhiro Hara, Takamatsu (JP); Makoto Ishizawa, Kagawa (JP)

(73) Assignee: National University Corporation Kagawa University, Kagawa (JP)

( * ) Notice: Subject to any disclaimer, the term of this patent is extended or adjusted under 35 U.S.C. 154(b) by 612 days.

(21) Appl. No.: 17/258,582

(22) PCT Filed: May 24, 2019

(86) PCT No.: PCT/JP2019/020762
§ 371 (c)(1),
(2) Date: Jan. 7, 2021

(87) PCT Pub. No.: WO2020/012793
PCT Pub. Date: Jan. 16, 2020

(65) Prior Publication Data
US 2021/0161412 A1 Jun. 3, 2021

(30) Foreign Application Priority Data

Jul. 10, 2018 (JP) ................................. 2018-131025

(51) Int. Cl.
*A61B 5/024* (2006.01)
*A61B 5/00* (2006.01)
(Continued)

(52) U.S. Cl.
CPC ........ *A61B 5/02405* (2013.01); *A61B 5/7225* (2013.01); *A61B 5/7257* (2013.01);
(Continued)

(58) Field of Classification Search
CPC .... A61B 5/7257; A61B 5/02405; A61B 5/361
See application file for complete search history.

(56) References Cited

U.S. PATENT DOCUMENTS

2005/0288725 A1 12/2005 Hettrick et al.
2012/0029361 A1* 2/2012 Addison ............ A61B 5/02125
600/484
(Continued)

FOREIGN PATENT DOCUMENTS

JP 2008504888 A 2/2008
JP 2014042547 A 3/2014
(Continued)

OTHER PUBLICATIONS

Hayano et al., "Spectral characteristics of ventricular response to atrial fibrillation", AJP Heart, Dec. 1997, pp. H2811-H2816, vol. 273, No. 6.

*Primary Examiner* — Yi-Shan Yang
*Assistant Examiner* — Om Patel
(74) *Attorney, Agent, or Firm* — The Webb Law Firm

(57) ABSTRACT

Provided are a pulse wave signal analyzer and an analysis method capable of determining a state of atrial fibrillation. The analyzer comprises a pulse wave detection unit for non-invasively detecting a pulse wave signal according to heartbeat of a living body; a spectrum generation unit for generating a frequency spectrum by Fourier transforming signal detected by the pulse wave detection unit; and an atrial fibrillation detection unit for detecting a state of atrial fibrillation based on the frequency spectrum generated by the spectrum generation unit. The spectrum generation unit repeatedly performs Fourier transform of the pulse wave signal at a predetermined time frame while shifting the time frame in a range of 0.005 to 0.02 seconds. The analyzer further comprises a filter for filtering the signal detected by
(Continued)

the pulse wave detection unit, and the spectrum generation unit generates the frequency spectrum from signal output from the filter.

19 Claims, 10 Drawing Sheets

(51) Int. Cl.
    *G16H 40/67*         (2018.01)
    *G16H 50/70*         (2018.01)

(52) U.S. Cl.
    CPC ............. *G16H 40/67* (2018.01); *G16H 50/70* (2018.01); *A61B 5/02444* (2013.01)

(56) References Cited

U.S. PATENT DOCUMENTS

| | | |
|---|---|---|
| 2013/0060154 A1 | 3/2013 | Morita |
| 2014/0257123 A1 | 9/2014 | Watanabe |
| 2016/0302680 A1 | 10/2016 | Narusawa et al. |
| 2017/0027459 A1 | 2/2017 | Shimuta |
| 2018/0014742 A1* | 1/2018 | Iwawaki ................. A61B 5/02 |
| 2018/0160926 A1* | 6/2018 | Chang ................... A61B 5/361 |

FOREIGN PATENT DOCUMENTS

| | | |
|---|---|---|
| JP | 2014171660 A | 9/2014 |
| JP | 2016083367 A | 5/2016 |
| JP | 2016202348 A | 12/2016 |
| JP | 2017042386 A | 3/2017 |
| JP | 2018011948 A | 1/2018 |
| WO | 2015159692 A | 10/2015 |

\* cited by examiner

PULSE-WAVE SIGNAL ANALYSIS DEVICE, PULSE-WAVE SIGNAL ANALYSIS METHOD AND COMPUTER PROGRAM

CROSS-REFERENCE TO RELATED APPLICATIONS

This application is the United States national phase of International Application No. PCT/JP2019/020762 filed May 24, 2019, and claims priority to Japanese Patent Application No. 2018-131025 filed Jul. 10, 2018, the disclosures of which are hereby incorporated by reference in their entirety.

BACKGROUND OF THE INVENTION

Field of the Invention

The present invention relates to a pulse wave signal analyzer, a pulse wave signal analysis method and a computer program, and more particularly to a pulse wave signal analyzer using a pulse wave detection function added to an automatic blood pressure monitor and the like, a pulse wave signal analysis method and a computer program.

Description of Related Art

Atrial fibrillation is a type of arrhythmia in which the entire atrium is excited and contracted very quickly in small steps, and the excitement is randomly transmitted to ventricles, impairing the contraction and expansion of the heart and losing regular beating.

Prolonged atrial fibrillation can lead to impaired heart function. In addition, atrial fibrillation makes it easier for blood clots to form, and the blood clots move into the brain by blood flow, increasing the risk of cerebral infarction.

Statistically, it is said that 3 to 5% of patients with atrial fibrillation develop cerebral infarction annually. Furthermore, since the prevalence of atrial fibrillation increases with age, atrial fibrillation is considered to be an important disease among heart diseases. Therefore, early detection of atrial fibrillation and initiation of appropriate treatment are important for the prevention of cardiogenic cerebral infarction.

Atrial fibrillation can be detected by electrocardiography. For example, Patent Documents 1 and 2 and Non-Patent Document 1 describe the use of electrocardiography for detection and classification of atrial arrhythmias. An electrocardiogram test is a method of measuring a heart rate by electrical pulses generated in the body for each cardiac cycle. However, the electrocardiogram test must be performed at a medical examination, a human dock, or the like, which is time-consuming and complicated. In addition, since the test described in Patent Document 1 is invasive, it is necessary to consider infection control and safety.

CITATION LIST

Patent Literature

Patent Document 1: Japanese Patent Publication No. 2008-504888
Patent Document 2: Japanese Patent Application Laid-open No. 2018-11948
Patent Document 3: Japanese Patent Application Laid-open No. 2014-42547

Non-Patent Literature

Non-patent Document 1: "Spectral characteristics of ventricular response to atrial fibrillation," American Physiological Society, 1997

SUMMARY OF THE INVENTION

Patent Document 3 discloses that atrial fibrillation is determined using arterial pulsation, that is, a pulse wave signal. The average pulse wave RR interval obtained by averaging the pulse wave signals is calculated, and frequency analysis is performed on this RR pulse wave interval. However, this method requires long-term measurement and complicated calculations because it is necessary to smooth out small fluctuations and to obtain the degree of variation with respect to the average pulse wave RR interval. Therefore, there is a demand for a method for accurately determining atrial fibrillation in a short time.

Also, there are individual differences in the symptoms of atrial fibrillation, and it is estimated that 40% of those suffering from atrial fibrillation have no subjective symptoms. Further, some people may feel palpitations and do not mind the symptoms. Thus, if there are no subjective symptoms of atrial fibrillation, or if a client does not mind the symptoms, the client may miss the opportunity to undergo a complicated test to find atrial fibrillation.

Moreover, in areas with poor medical service, it is difficult to undergo such tests. As a result of such circumstances, there is a problem that the symptom is left unattended and the opportunity for early detection and treatment is missed.

Furthermore, in the case of paroxysmal atrial fibrillation that occurs in the early stages of atrial fibrillation, atrial fibrillation may not be detected at the time of measurement due to the short period of the state of atrial fibrillation. Therefore, a simple inspection method capable of performing repeated inspections is desirable.

Therefore, a method for determining atrial fibrillation with a high probability by using a simple method other than the electrocardiography is desired.

The present invention has been made in view of such a problem, and an object of the present invention is to provide a pulse wave signal analyzer, a pulse wave signal analysis method and a computer program which can accurately determine the state of atrial fibrillation by a simple method.

In order to solve the above problems, according to one aspect of the embodiment, there is provided a pulse wave signal analyzer, including: a signal detection means for non-invasively detecting a pulse wave signal according to heartbeat of a living body; a generation means for generating a frequency spectrum by Fourier transforming the pulse wave signal detected by the signal detection means; and an analysis means for detecting a state of atrial fibrillation based on the frequency spectrum generated by the generation means, in which the generation means repeatedly performs Fourier transform of the pulse wave signal at a predetermined time frame while shifting the time frame in a range of 0.005 seconds to 0.02 seconds.

Here, the analyzer can further comprise a filter for filtering the pulse wave signal detected by the signal detecting means, and the generation means can generate the frequency spectrum from the pulse wave signal output from the filter.

In addition, the analysis means can detect the state of atrial fibrillation when a frequency component corresponding to a cycle of the heartbeat does not have a plurality of peaks in the frequency spectrum.

Further, the predetermined time frame can be 2 to 4 seconds.

Furthermore, the signal detecting means can detect the pulse wave signal of a pressure pulse wave.

In addition, the analysis means can detect the state of atrial fibrillation based on a time change of the frequency spectrum.

Here, the analysis means can detect the state of atrial fibrillation based on time duration of a predetermined number of peaks.

Here, the analysis means can detect the state of atrial fibrillation further based on an amount in which a frequency of the peak fluctuates.

Here, the analysis means can detect the state of atrial fibrillation based on two or more of time duration of a peak at a given frequency, frequency variation of the peak, and a number of occurrences of temporally discontinuous peaks.

According to another aspect of the embodiment, there is provided a pulse wave signal analysis method, including the steps of: non-invasively detecting a pulse wave signal according to heartbeat of a living body; generating a frequency spectrum by Fourier transforming the pulse wave signal detected by the signal detection means; and detecting a state of atrial fibrillation based on the frequency spectrum generated by the generation means, in which the generating step repeatedly performs Fourier transform of the pulse wave signal at a predetermined time frame while shifting the time frame in a range of 0.005 seconds to 0.02 seconds.

Here, the method can further include the step of filtering the pulse wave signal detected by the signal detecting means, and the generating step can include generating the frequency spectrum from the filtered pulse wave signal.

Further, the step of detecting the state of atrial fibrillation can include detecting the state of atrial fibrillation when a frequency component corresponding to a cycle of the heartbeat does not have a plurality of peaks in the frequency spectrum.

Further, the predetermined period can be 2 to 4 seconds.

In addition, the step of detecting the state of atrial fibrillation can detect the pulse wave signal of a pressure pulse wave.

Further, the step of detecting the state of atrial fibrillation can detect the state of atrial fibrillation based on a time change of the frequency spectrum.

Here, the step of detecting the state of atrial fibrillation can detect the state of atrial fibrillation based on time duration in which a predetermined number of peaks lasts.

In addition, the step of detecting the state of atrial fibrillation can detect the state of atrial fibrillation based on an amount in which a frequency of the peak fluctuates.

Further, the step of detecting the state of atrial fibrillation can detect the state of atrial fibrillation based on two or more of time duration of a peak at a given frequency, frequency variation of the peak, and a number of occurrences of temporally discontinuous peaks.

According to another aspect of the embodiment, there is provided a computer program that causes a computer to function as the above-mentioned pulse wave signal analyzer.

According to the other aspect of the embodiment, there is provided a computer-readable storage medium that stores the above-mentioned computer program.

According to the present disclosure, the pulse wave signal is detected non-invasively, and the detected pulse wave signal is repeatedly subjected to Fourier transform for a predetermined period while shifting in the range of 0.005 seconds to 0.02 seconds to obtain a frequency. Generate a spectrum and detect the state of atrial fibrillation based on the generated frequency spectrum. Therefore, the state of atrial fibrillation can be easily detected.

In addition, since the state of atrial fibrillation can be detected by a simple method, the probability of detecting paroxysmal atrial fibrillation is improved by performing repeated examinations.

Further, by detecting the pulse wave signal using the pressure pulse wave, highly reliable data can be obtained in a short time by using the sphygmomanometer.

DETAILED DESCRIPTION OF THE INVENTION

Hereinafter, embodiments of the present invention will be described in detail with reference to the drawings. In the following description, a pulse wave refers to the waveform of a volume change of a body part caused by a beating of a heart. Among the pulse waves, those due to changes in blood pressure are referred to as pressure pulse waves, those due to changes in volume are referred to as volumetric pulse waves, and any of these is included in the present embodiment.

Figure 1:
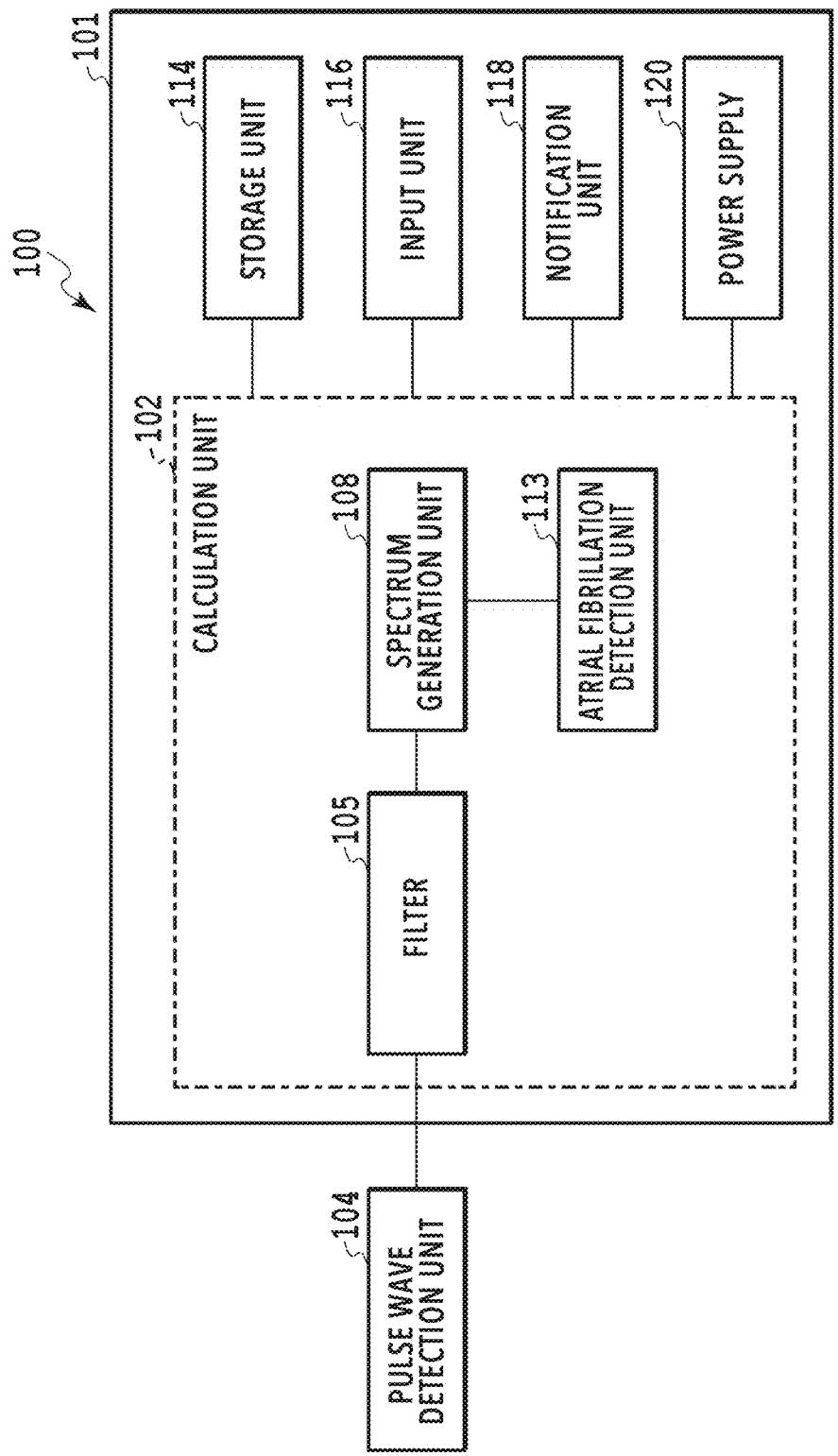
FIG. 1 is a block diagram showing a functional configuration of a pulse wave analyzer according to an embodiment.

FIG. 1 is a block diagram showing a functional configuration of a pulse wave analyzer according to an embodiment of the present invention. An analyzer 100 functions as a diagnostic device for atrial fibrillation, and is configured so that a pulse wave detection unit 104 and an analysis unit 101 can be connected to communicate signals. In this case, the communication means may be wired or may be compliant with a wireless communication standard such as Bluetooth (registered trademark). The pulse wave detection unit 104 and the analysis unit 101 may be integrated into one device, may be configured separately, or may be configured to be detachable from each other.

The analysis unit 101 includes a calculation unit 102, a storage unit 114, an input unit 116, a notification unit 118, and a power supply 120.

The pulse wave detection unit 104 non-invasively detects a pulse wave signal according to the heartbeat of a living body, and may be configured as a contact type or non-contact type biological sensor. For example, the analyzer 100 can be configured as a sphygmomanometer, in which case the pulse wave detection unit 104 is configured to include a cuff to be wrapped around a predetermined portion of an arm. The cuff is provided with an inflatable bag-shaped member. The sphygmomanometer is preset with a compression pressure for blocking blood flow in an artery located inside a cuff wrapped around the arm or the like. When detecting a pulse wave, the blood pressure is measured by increasing the pressure inside the bag-shaped member to the compression pressure and then gradually lowering the pressure at a predetermined speed. Since blood vessels compressed by the cuff vibrate in accordance with the heartbeat, the pressure inside the bag-shaped member is sequentially detected in the process of lowering the blood pressure in blood pressure measurement, and the pulse wave is detected from a pressure change.

The pulse wave detection unit 104 may be configured as a combination of a sphygmomanometer and a wireless electrocardiographic transmitter, and the analyzer 100 may be configured as an information processing device such as a personal computer. In this case, the pulse wave detection unit 104 may include an input unit such as a button for instructing execution of an operation for measuring blood pressure, and a display unit for displaying the measurement result.

Alternatively, the pulse wave detection unit 104 may be configured by any other sensor such as of a tactile sensor or the like, which measures the pulse wave signal by the pressure.

Alternatively, the analyzer 100 may be configured as a fingertip pulse wave detector including a pulse oximeter or the like that measures oxygen saturation using laser light. In this case, the pulse wave detection unit 104 detects the pulse wave by irradiating Infrared laser to hands and feet fingertip and measuring changes in the volume of blood flowing through the fingertips.

Alternatively, the analyzer 100 may be configured as a non-contact device such as a camera or a mobile terminal. In this case, the pulse wave detection unit 104 detects the pulse wave by measuring change in brightness caused by the blood flow based on the captured image.

Alternatively, the analyzer 100 may be configured as another optical heart rate monitor. In this case, the pulse wave detection unit 104 includes an optical heart rate sensor. The pulse wave detection unit 104 irradiates light using an LED to a predetermined position such as an arm, and detects the pulse wave by measuring an amount of scattered light reflected by the blood flow.

Next, various functions of the analysis unit 101 will be described. The calculation unit 102 performs calculation processing based on an electric signal of the pulse wave output from the pulse wave detection unit 104, and is composed of one or more processors. The calculation unit 102 is further communicably connected to the storage unit 114, the input unit 116, and the notification unit 118. The storage unit 114 is configured to store a program for executing the processing according to the present embodiment, data used in arithmetic processing, or arithmetic result data. Specifically, the storage unit 114 may be configured as a USB flash drive, a removable hard disk, a read-only memory (ROM), a random access memory (RAM), a magnetic disk, an optical disk, or the like.

The input unit 116 is configured as a keyboard, buttons, dials or switches for inputting commands and information of set values for information processing from a user, an input interface for inputting data, and the like. The notification unit 118 is configured as a liquid crystal display, a lamp, a speaker, or the like for outputting notification information based on the calculation result of the calculation unit 102. In addition, the analyzer 100 includes the power supply 120 for supplying power to each component in the device.

Next, each component included in the calculation unit 102 will be described. The calculation unit 102 includes a filter 105, a spectrum generation unit 108, and an atrial fibrillation detection unit 113.

The filter 105 is for passing frequencies associated with pulse waves. The frequency passed here can be a frequency equal to or lower than an audible frequency. The filter 105 may also be configured as a low frequency filter designed to remove high frequency pressure signals that are considered to be associated with atrial flutter.

The spectrum generation unit 108 performs a Fourier transform on time series data of the pulse wave signal in order to perform spectrum analysis. As the Fourier transform, for example, a fast Fourier transform (FFT) may be performed. As a result, the spectrum generation unit 108 acquires a frequency spectrum of a signal waveform. It should be noted that the fast Fourier transform is an example, and another Fourier transform for generating the frequency spectrum can be used.

The atrial fibrillation detection unit 113 is configured to analyze the signal waveform, and at least detects a state of atrial fibrillation in the living body from the frequency spectrum acquired by the spectrum generation unit 108.

In addition, one or more functions included in the calculation unit 102 in the analysis unit 101 may be implemented in the pulse wave detection unit 104. For example, the pulse wave detection unit 104 may be provided with the function of the filter 105, and the pulse wave signal filtered by the pulse wave detection unit 104 may be supplied to the calculation unit 102.

Figure 2:
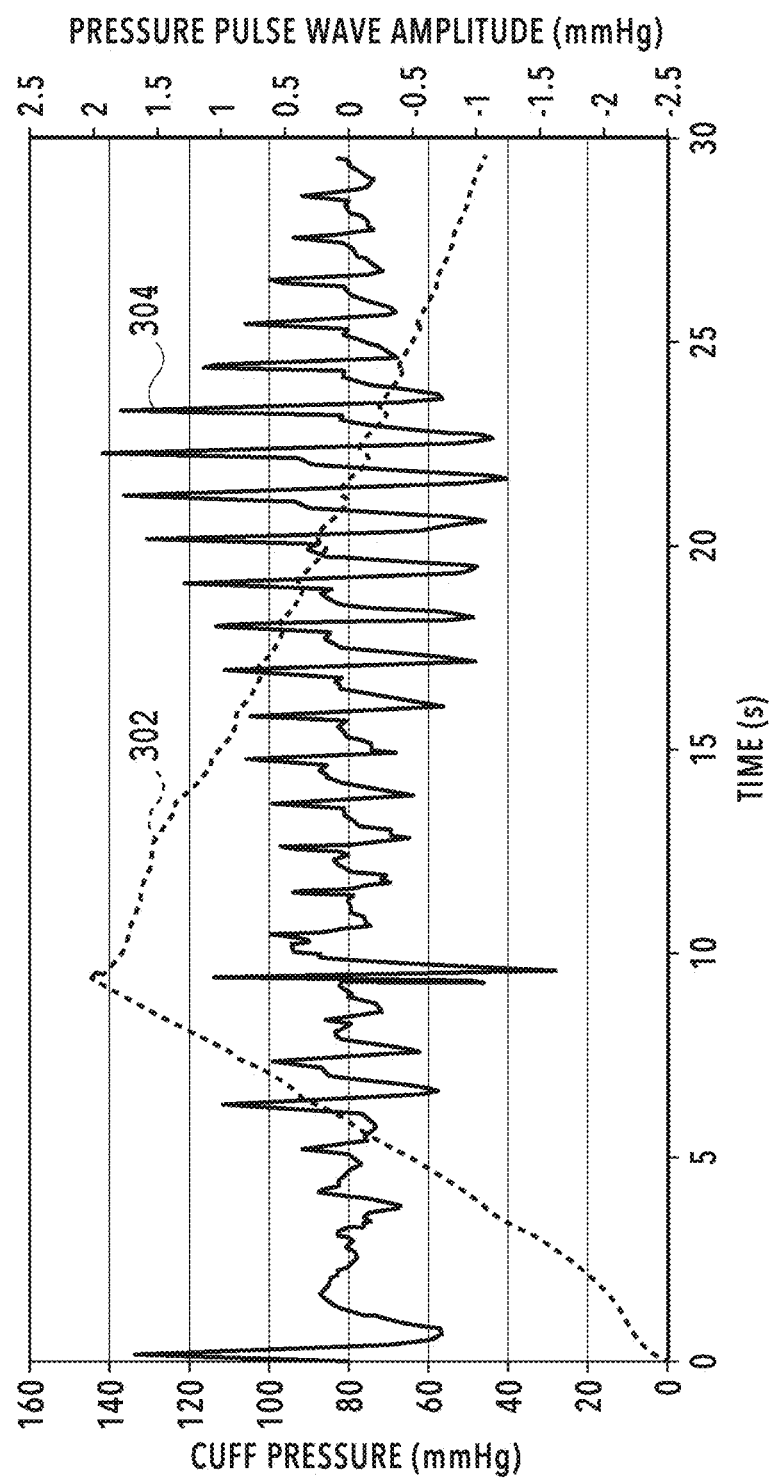
FIG. 2 is a diagram showing an example of values detected by an analyzer 100.

Next, the detection process of atrial fibrillation will be specifically described. As an example, a case where the pulse wave detection unit 104 is configured as a combination of an electrocardiographic transmitter and an automatic sphygmomanometer to measure an electrocardiogram and blood pressure simultaneously will be described. FIG. 2 shows an example of values detected by the analyzer 100. In the figure, the horizontal axis represents time (s). The curved broken line 302 shows a cuff pressure (mmHg) of the automatic blood pressure monitor, and the curved solid line 304 shows an amplitude of the pressure pulse wave (mmHg) output from the electrocardiographic transmitter. During the period when an internal pressure of the blood vessel exceeds the pressure of the cuff, the blood vessel dilates, and change in the volume of the blood vessel increases the internal pressure of the cuff. In the oscillometric method, blood pressure is obtained by observing fluctuations in cuff pressure synchronized with the heartbeat in the process of decompressing the cuff. The fluctuation of the cuff pressure observed here is measured as a pressure pulse wave.

The pulse wave waveform obtained from the patient is filtered. The filtered waveform is then Fourier transformed. The section to be converted here is preferably about 2 to 20 seconds. In this section, data having a frame time (interval)

of 2 to 4 seconds is acquired at a frequency of 50 to 200 times per second (every 0.005 to 0.02 second) while shifting the time axis.

The atrial fibrillation detection unit 113 analyzes the value of the frequency spectrum output from the spectrum generation unit 108. For example, as shown in FIG. 4(b), when there are two or three distinct peaks at equal intervals on the horizontal axis, it is detected that the patient is not in a state of atrial fibrillation (negative). Here, the "peak" of the frequency spectrum refers to the peak of the amplitude of the pressure pulse wave. Specifically, this peak exists at the position of the frequency component of the fundamental frequency corresponding to a cycle of the heartbeat of the living body and its harmonic. On the other hand, as shown in FIG. 7(b), when the value of the frequency spectrum does not have a clear peak at the position of the frequency component corresponding to the cycle of the heartbeat, the state of atrial fibrillation (positive) is detected.

Figure 3:
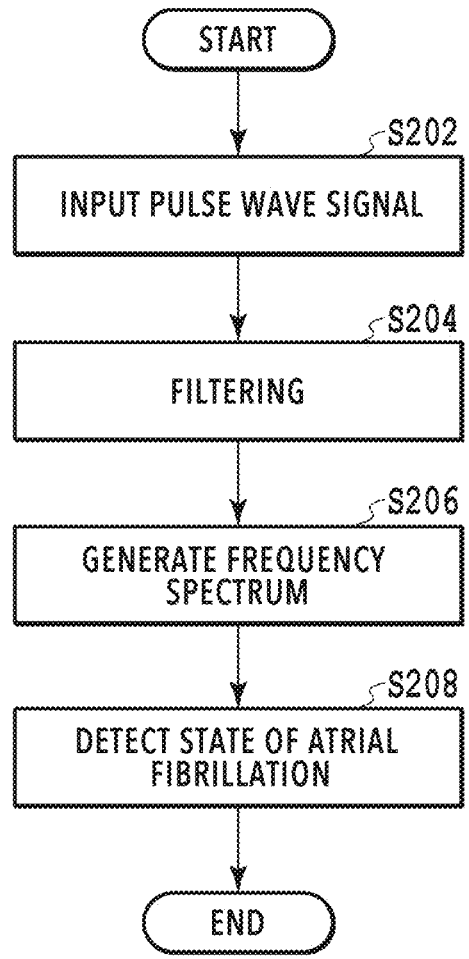
FIG. 3 is a flowchart showing a procedure of a method for detecting atrial fibrillation according to an embodiment.

Next, a method for detecting atrial fibrillation executed by the analyzer according to the present embodiment will be described with reference to the flowchart of FIG. 3.

First, in step S202, the analysis unit 101 inputs the pulse wave signal of the living body from the pulse wave detection unit 104. In step S204, the filter 105 performs filtering to pass frequencies associated with the pulse wave. In step S206, the spectrum generation unit 108 inputs the time series data of the signal input from the filter 105, performs a fast Fourier transform, and acquires a frequency spectrum.

In step S208, the atrial fibrillation detection unit 113 detects that the living body is in the state of atrial fibrillation (positive) from the frequency spectrum acquired by the spectrum generation unit 108. Specifically, if the frequency spectrum does not have a clear peak in the frequency component corresponding to the heartbeat cycle, it is detected that the patient is in the state of atrial fibrillation (positive), and if it has a clear peak in the frequency component corresponding to the heartbeat cycle, it is detected that the patient is not in the state of atrial fibrillation (negative). After that, when the state of atrial fibrillation is detected, the analysis unit 101 stores the detection result in the storage unit 114, notifies through the notification unit 118 that atrial fibrillation may have occurred, and ends the process.

EXAMPLES

Example 1

Next, examples of the present invention will be described. This example targeted patients with sinus rhythm, persistent atrial fibrillation or extrasystoles. As a component corresponding to the pulse wave detection unit 104, Health Patch MD (electrocardiographic transmitter) and a HEM-6310F/M6 (automatic sphygmomanometer) manufactured by OMRON HEALTHCARE Co., Ltd. were used. In addition, a personal computer was used as a configuration corresponding to the analysis unit 101. Then, with reference to FIG. 2, simultaneous measurement of the above-mentioned electrocardiogram and blood pressure was performed on a total of 280 subjects (sinus rhythm: 197, atrial fibrillation: 40, other arrhythmias: 43).

Next, the pulse wave waveform obtained from the patient was subjected to a fast Fourier transform to obtain a frequency spectrum. Since the automatic sphygmomanometer takes about 20 to 30 seconds for a measurement of blood pressure and pulse rate, the entire 20 to 30 seconds was used as the analysis target of the fast Fourier transform.

Figure 4:
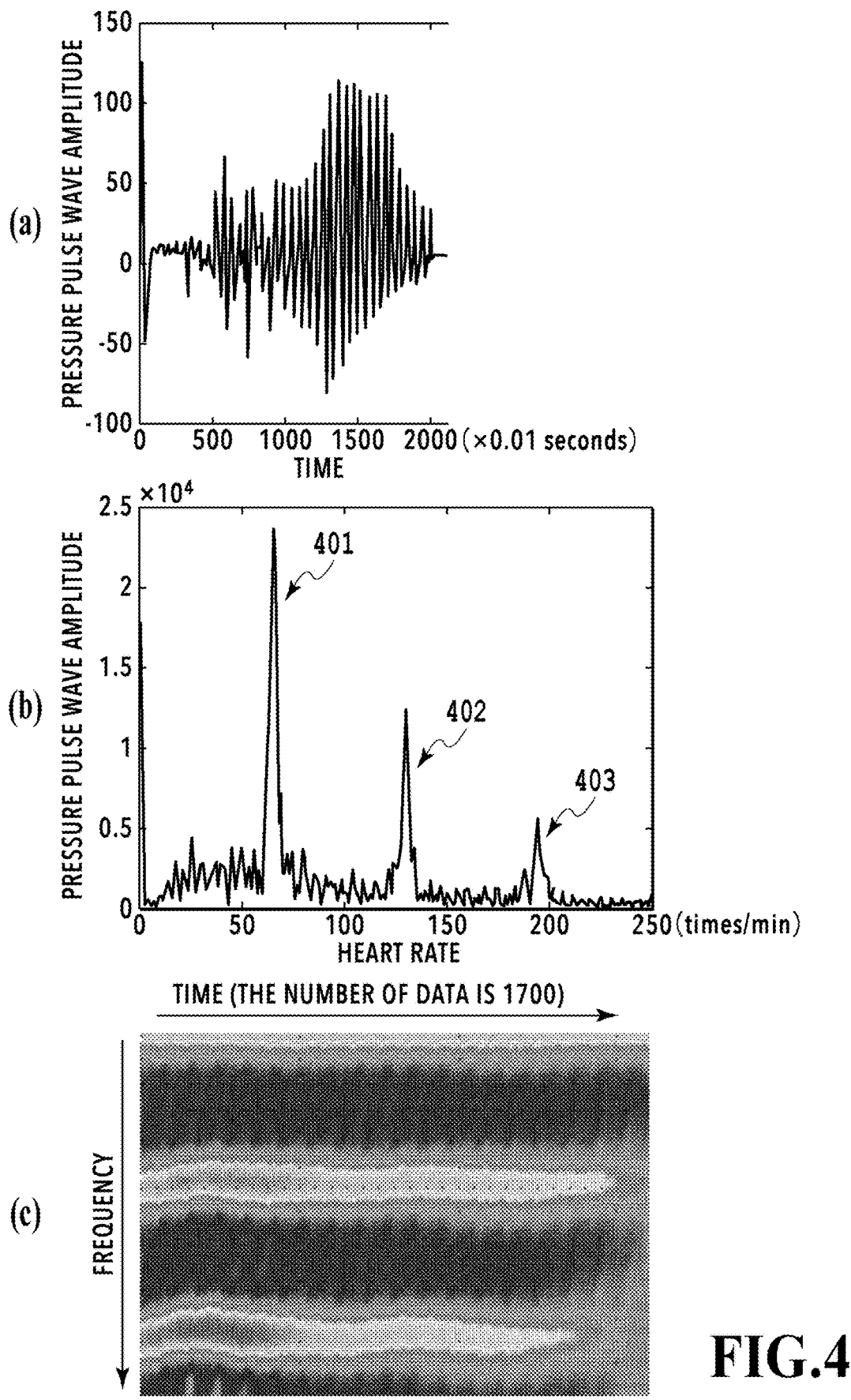
FIG. 4 (*a*) is a measurement result of pulse wave waveform according to an embodiment, (b) is a diagram after a fast Fourier transform, and (c) is a diagram showing a time change of the result of the fast Fourier transform.

FIG. 4 shows the measurement results obtained for patients with sinus rhythm. (a) is a pulse wave waveform in which the horizontal axis is time (×0.01 second) and the vertical axis is the amplitude of pressure pulse wave. Further, (b) shows a figure after the fast Fourier transform in which the horizontal axis shows the heart rate (times/minute) and the vertical axis shows the amplitude of the pressure pulse wave. Since the number of samplings of the data measured by the automatic sphygmomanometer was small, the actual number of horizontal axis data was increased about 100 times in order to match characteristics of an electronic circuit for the fast Fourier transform. In the frequency spectrum diagram shown in FIG. 4(b), an arrow 401 indicates a peak of a fundamental wave, and arrows 402 and 403 indicate the peak of the harmonic band. As shown in the figure, sharp peak waveforms with three peaks of frequency is observed in patients with sinus rhythm, in about 65 (times/minute) corresponding to the heartbeat cycle, and about 130 (times/minute) and about 190 (times/minute) which are the harmonic bands thereof.

Figure 5:
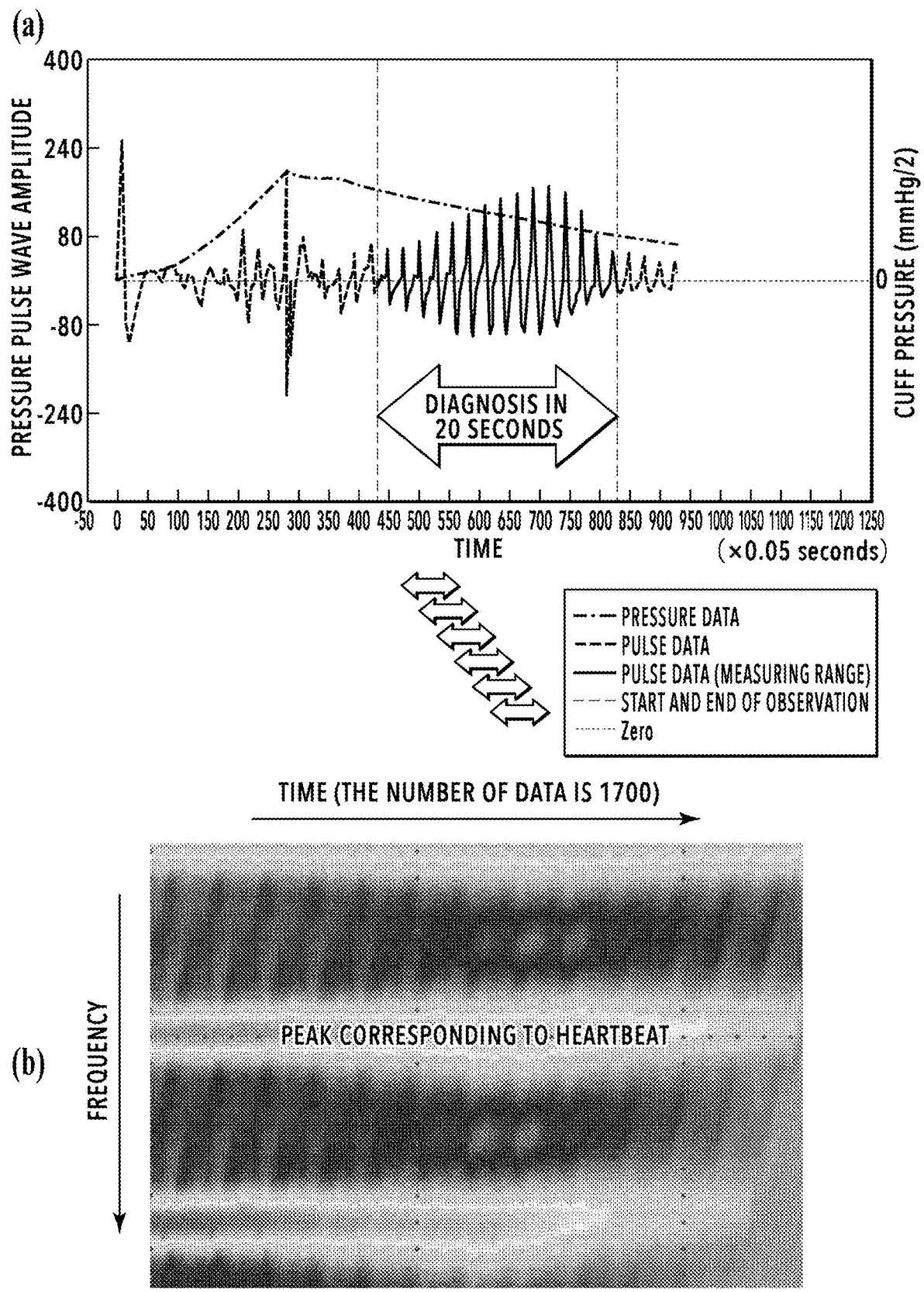
FIG. 5 is diagrams showing a method of creating a diagram showing a time change of the result of Fourier transform, in which (a) is a pulse wave waveform and (b) is a created diagram.

FIG. 4(c) is a diagram showing a time change of the result of the fast Fourier transform. The method of creating this figure will be described with reference to FIG. 5. FIG. 5(a) shows a pulse wave waveform, with the horizontal axis representing time (seconds/20) and the vertical axis representing cuff pressure (mmHg/2). A range of 20 seconds was specified in the pulse wave waveform, and the Fourier transform with a frame time of 3 seconds was repeated in this range while shifting by 0.01 seconds. Next, 17 seconds were cut out from the obtained Fourier transform results, arranged on the time axis, and the peaks of the heartbeat information were mapped to obtain the graph shown in FIG. 5 (b). In FIG. 5(b), the horizontal axis represents time, and 1700 pieces (17 seconds/0.01 seconds=1700) of data are arranged. The vertical axis shows frequency. Spectral intensity in the result of the Fourier transform is represented by the shade of color, with the highest value being 1 and the range of 0.8 to 0.9 represented by shade.

Figure 6:
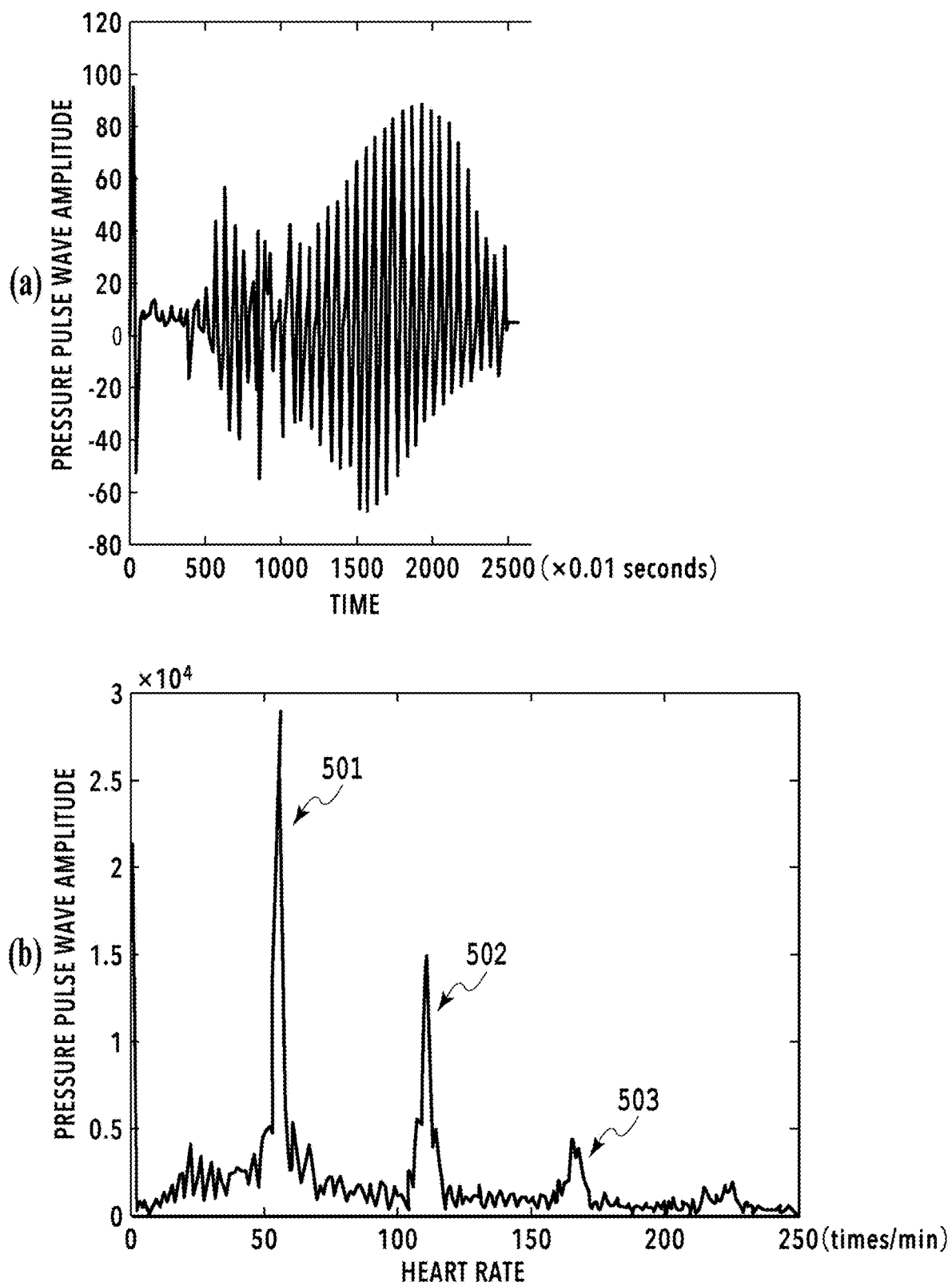
FIG. 6 (*a*) is a pulse wave waveform of a measurement result according to an embodiment, and (b) is a diagram after fast Fourier transform.

FIG. 6 shows the measurement results obtained for another patient of sinus rhythm, in which (a) shows the pulse wave waveform, and (b) shows the figure after the fast Fourier transform. In the frequency spectrum diagram shown in FIG. 6(b), an arrows 501 indicates a peak of the fundamental wave, and arrows 502 and 503 indicate peaks of the harmonic band. Also in the figure, as in FIG. 4, sharp peak waveforms with three peaks of frequency is observed in about 55 (times/minute) corresponding to the patient's heartbeat cycle, and about 110 (times/minute) and about 165 (times/minute) which are the harmonic bands thereof.

Figure 7:
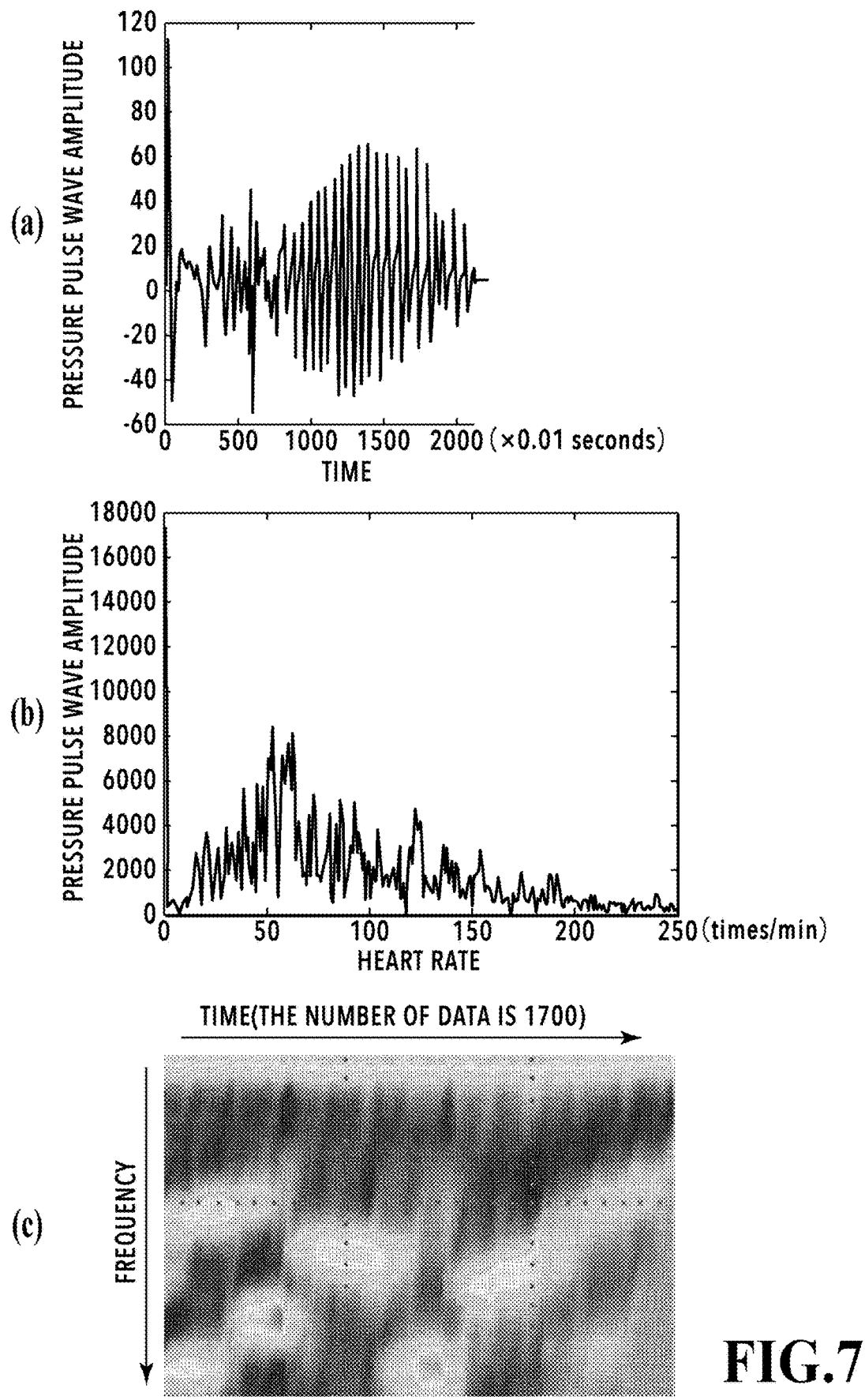
FIG. 7 (*a*) is a pulse wave waveform of a measurement result according to an embodiment, (b) is a diagram after a fast Fourier transform, and (c) is a diagram showing a time change of the result of the fast Fourier transform.

FIG. 7 shows the measurement results obtained for the patient with atrial fibrillation, in which (a) shows the pulse wave waveform, (b) shows the figure after the fast Fourier transform, and (c) shows a time change of the result of the fast Fourier transform. In the frequency spectrum diagram shown in FIG. 7(b), the sharp peak waveforms with three peaks disappeared.

Figure 8:
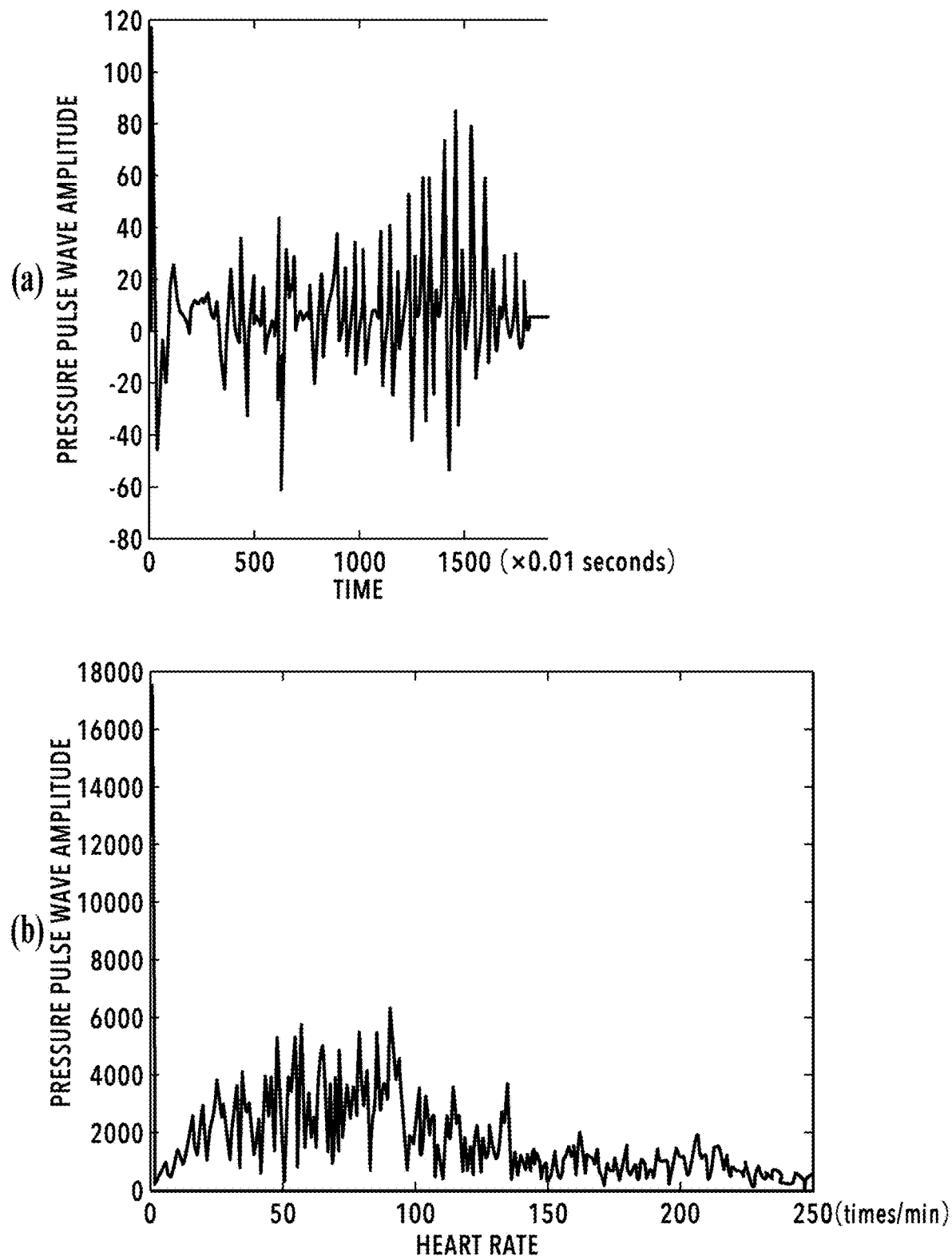
FIG. 8 (*a*) is a pulse wave waveform of a measurement result according to an embodiment, and (b) is a diagram after fast Fourier transform.

FIG. 8 shows the measurement results obtained for another patient with atrial fibrillation, in which (a) shows the pulse wave waveform, and (b) shows the figure after the fast Fourier transform. In the frequency spectrum diagram shown in FIG. 8 (b), the sharp peak waveforms with three peaks disappeared as in FIG. 7.

Figure 9:
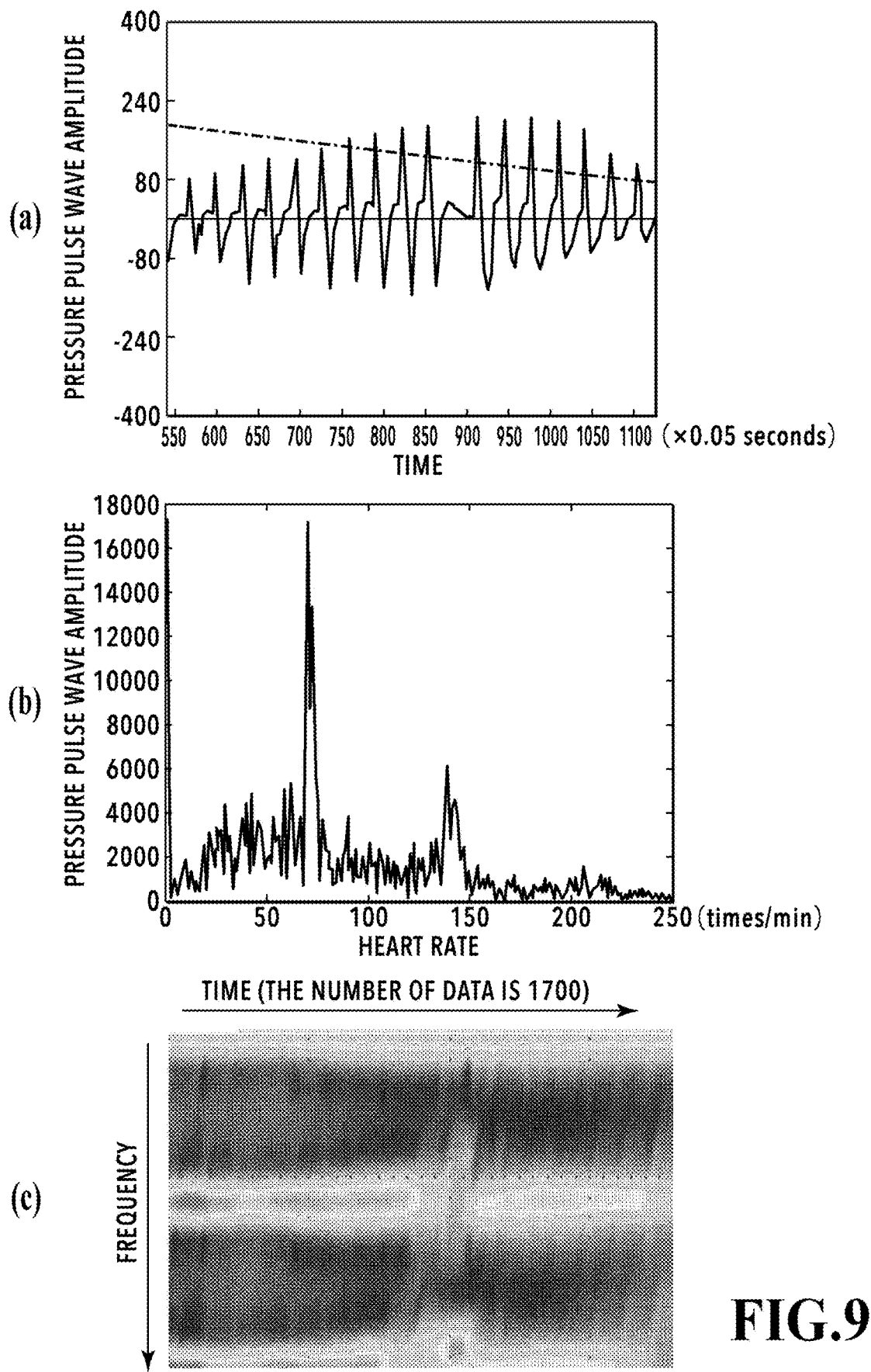
FIG. 9 (*a*) is a pulse wave waveform of a measurement result according to an embodiment, (b) is a diagram after a fast Fourier transform, and (c) is a diagram showing a time change of the result of the fast Fourier transform.

FIG. 9 shows the measurement results obtained for the patient with extra systole, in which (a) shows the pulse wave waveform, (b) shows the figure after the fast Fourier transform, and (c) shows a time change of the result of the fast Fourier transform. In the frequency spectrum diagram shown in FIG. 9 (b), two-peak waveforms are found in about 70 (times/minute) corresponding to the patient's heartbeat cycle and about 140 (times/minute) which is the harmonic band thereof.

When the above consideration was applied to the measurement results of other patients, it was found that the following judgment can be made. That is, according to the measurement results of patients with atrial fibrillation, there is no clear peak in the frequency component corresponding to the cycle of the patient's heartbeat in the frequency spectrum. On the other hand, the measurement results of patients without atrial fibrillation have multiple clear peaks. The positions of these peaks correspond to frequency components of the fundamental frequency that corresponds to the patient's heartbeat cycle and its harmonic.

Example 2

Figure 10:
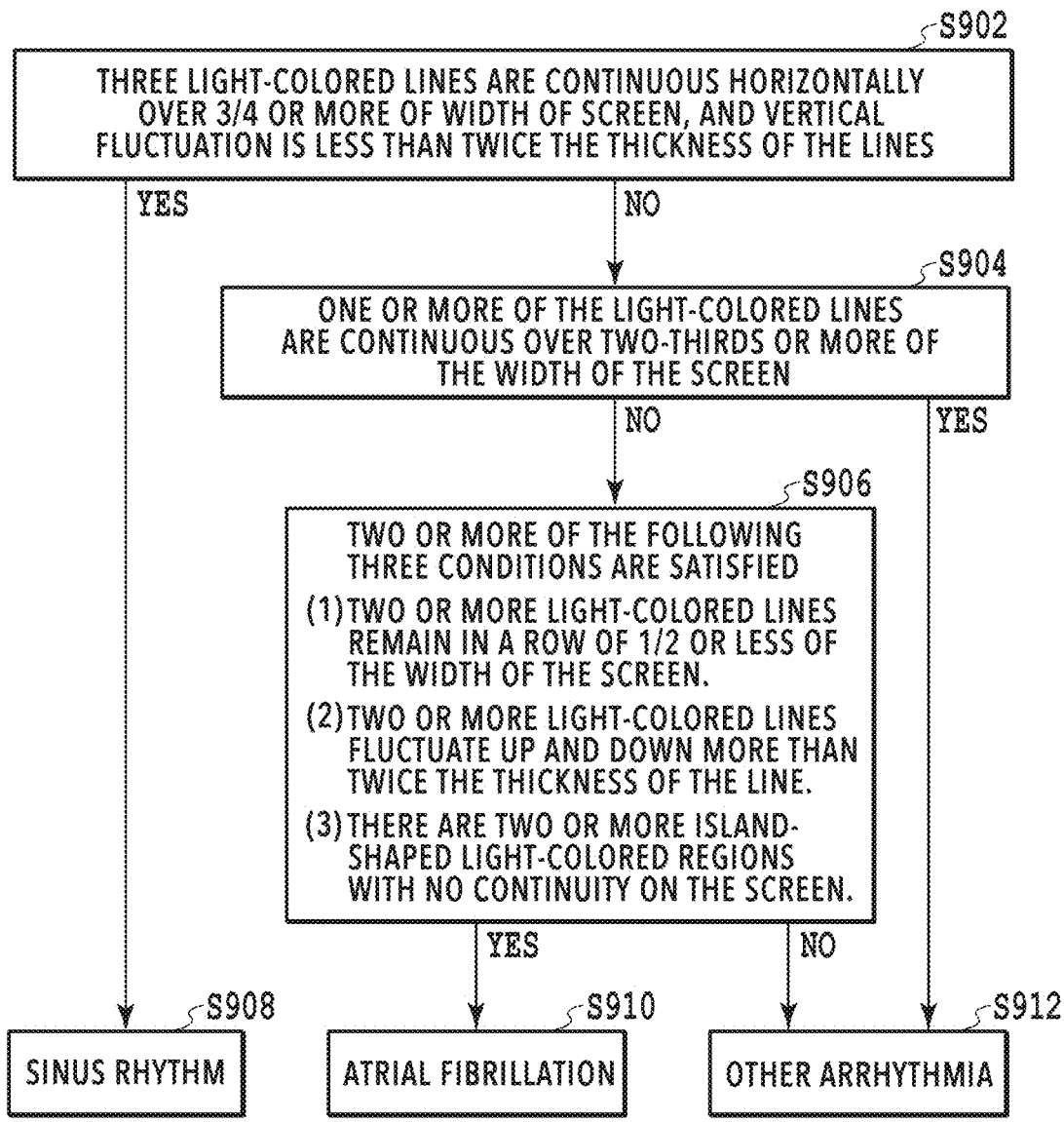
FIG. 10 is a diagram showing a flow of a method for determining atrial fibrillation according to an embodiment.

The images shown in FIGS. 4 (c), 7 (c), and 9 (c) obtained in the above-described examples were analyzed, and atrial fibrillation was determined as shown in FIG. 10.

First, determination was made based on time duration of a predetermined number of peaks and amount of fluctuation of the peak frequency. That is, it was determined whether three light-colored lines were continuous horizontally over ¾ or more of the width of the screen in the image, and the vertical fluctuation was less than twice the thickness of the lines (S902). When this condition was met, it was determined to be sinus rhythm (S908).

When the condition of step S902 was not met, the next determination was made based on the time duration of a predetermined number of peaks. Specifically, it was determined whether one or more of the light-colored lines were continuous over two-thirds or more of the width (S904). When this condition was met, it was determined to be an arrhythmia other than atrial fibrillation (S912).

Then, if the condition of step S904 was not met, the next determination was made based on two or more of the time duration of the peak at a predetermined frequency, the fluctuation of the frequency of the peak, and the number of occurrences of temporally discontinuous peaks. Specifically, it was determined whether or not two or more of the following three conditions were satisfied (S906).
 (1) Two or more light-colored lines remain in a row of ½ or less of the width of the screen.
 (2) Two or more light-colored lines fluctuate up and down more than twice the thickness of the line.
 (3) There are two or more island-shaped light color regions with no continuity on the screen.

When the condition of S906 was met, it was determined to be atrial fibrillation.

In this example, the measurement results of 280 persons were observed, and the case where atrial fibrillation was determined 2 or more times out of 3 measurements was determined to be positive. As a result, the above characteristics were applied to all of the measurement results.

Although the embodiment of the present invention has been described above, the apparatus according to the present embodiment, its components, and the steps of the method described above can be carried out by hardware or by a combination of software and hardware. Whether functions of the device or its components are performed by hardware or software is subject to the constraints in design of the above embodiments. Although those skilled in the art can perform the functions of the components described above for specific applications using various methods, such changes are also within the scope of the present invention.

The apparatus described in the above embodiments is merely an example, and other methods can be used. For example, the above-mentioned components are logically divided functions, and the components may be divided by other methods in implementation. Further, two or more of the above-mentioned components may be integrated into one component, and each of the components may physically exist independently.

When the function described in the above embodiments is performed in the form of software, a computer program for realizing the function can be stored in a computer-readable storage medium. The computer program includes several instructions for instructing the computer to function as all or part of the components described in the above embodiments.

The invention claimed is:

1. A pulse wave signal analyzer, comprising:
 a pulse wave detection unit configured to non-invasively detect a pulse wave signal according to a heartbeat of a living body;
 a memory that stores executable instructions; and
 a processor configured to execute the instructions such that the processor is configured to:
  generate a frequency spectrum by performing a Fourier transform of the pulse wave signal detected by a single operation by the pulse wave detection unit for detecting the pulse wave signal; and
  detect a state of atrial fibrillation based on the generated frequency spectrum,
  wherein when generating the frequency spectrum, the processor is configured to repeatedly perform the Fourier transform of the pulse wave signal over a predetermined time frame while shifting the predetermined time frame in a range of 0.005 seconds to 0.02 seconds for each repeat of the Fourier transform.

2. The pulse wave signal analyzer according to claim 1, wherein the processor is further configured to filter the pulse wave signal, and wherein when generating the frequency spectrum, the processor is configured to generate the frequency spectrum from a pulse wave signal output from the filter.

3. The pulse wave signal analyzer according to claim 1, wherein when detecting the state of atrial fibrillation, the processor is configured to detect the state of atrial fibrillation when a frequency component corresponding to a cycle of the heartbeat does not have a plurality of peaks in the frequency spectrum.

4. The pulse wave signal analyzer according to claim 1, wherein the predetermined time frame is 2 to 4 seconds.

5. The pulse wave signal analyzer according to claim 1, wherein when non-invasively detecting the pulse wave signal, the processor is configured to detect the pulse wave signal of a pressure pulse wave.

6. The pulse wave signal analyzer according to claim 1, wherein when detecting the state of atrial fibrillation, the processor is configured to detect the state of atrial fibrillation based on a change of a plurality of frequency spectrums obtained by repeatedly performing the Fourier transform over time.

7. The pulse wave signal analyzer according to claim 6, wherein when detecting the state of the atrial fibrillation based on the change of the plurality of frequency spectrums, the processor is configured to detect the state of atrial fibrillation based on a time duration in which a predetermined number of peaks continuously occurs.

8. The pulse wave signal analyzer according to claim 7, wherein when detecting the state of atrial fibrillation based on the change of the plurality of frequency spectrums, the processor is configured to detect the state of atrial fibrillation further based on an amount in which a frequency of each of the peaks fluctuate.

9. The pulse wave signal analyzer according to claim 6, wherein when detecting the state of atrial fibrillation based on the change of the plurality of frequency spectrums, the processor is configured to detect the state of atrial fibrillation based on two or more of a time duration of a peak at a given frequency, a frequency variation of the peak, and a number of occurrences of temporally discontinuous peaks.

10. A pulse wave signal analysis method, comprising:
non-invasively detecting a pulse wave signal according to a heartbeat of a living body;
generating a frequency spectrum by performing a Fourier transform of the detected pulse wave signal detected by a single operation for detecting the pulse wave signal; and
detecting a state of atrial fibrillation based on the frequency spectrum,
wherein generating the frequency spectrum includes repeatedly performing the Fourier transform of the pulse wave signal over a predetermined time frame while shifting the predetermined time frame in a range of 0.005 seconds to 0.02 seconds for each repeat of the Fourier transform.

11. The pulse wave signal analysis method according to claim 10, further comprising filtering the detected pulse wave signal, and wherein generating the frequency spectrum includes generating the frequency spectrum from the filtered pulse wave signal.

12. The pulse wave signal analysis method according to claim 10, wherein detecting the state of atrial fibrillation includes detecting the state of atrial fibrillation when a frequency component corresponding to a cycle of the heartbeat does not have a plurality of peaks in the frequency spectrum.

13. The pulse wave signal analysis method according to claim 10, wherein the predetermined time frame is 2 to 4 seconds.

14. The pulse wave signal analysis method according to claim 10, wherein detecting the state of atrial fibrillation includes detecting the pulse wave signal of a pressure pulse wave.

15. The pulse wave signal analysis method according to claim 10, wherein detecting the state of atrial fibrillation includes detecting the state of atrial fibrillation based on a change of a plurality of frequency spectrums obtained by repeatedly performing the Fourier transform over time.

16. The pulse wave signal analysis method according to claim 15, wherein detecting the state of atrial fibrillation based on the change of the plurality of frequency spectrums includes detecting the state of atrial fibrillation based on a time duration in which a predetermined number of peaks continuously occurs.

17. The pulse wave signal analysis method according to claim 16, wherein detecting the state of atrial fibrillation based on the change of the plurality of frequency spectrums includes detecting the state of atrial fibrillation further based on an amount in which a frequency of each of the peaks fluctuate.

18. The pulse wave signal analysis method according to claim 15, wherein detecting the state of atrial fibrillation based on the change of the plurality of frequency spectrums includes detecting the state of atrial fibrillation based on two or more of a time duration of a peak at a given frequency, a frequency variation of the peak, and a number of occurrences of temporally discontinuous peaks.

19. A non-transitory computer-readable storage medium stored thereon a computer program that causes a computer to execute the pulse wave signal analysis method according to claim 10.

* * * * *